US012600708B2

(12) United States Patent
Hoyer et al.

(10) Patent No.: US 12,600,708 B2
(45) Date of Patent: Apr. 14, 2026

(54) PRODRUG COMPOUNDS OF 3,4-METHYLENEDIOXY-METHAMPHETAMINE (MDMA) AND METHODS OF SYNTHESIZING THE SAME

(71) Applicant: Mydecine Innovations Group Inc., Denver, CO (US)

(72) Inventors: Denton W. Hoyer, West Haven, CT (US); Robert F. Roscow, Longmont, CO (US); Rong Ling, Edmonton (CA); Chuanjun Gao, Edmonton (CA)

(73) Assignee: Apoapsis Holdings, LLC, Longmont, CO (US)

( * ) Notice: Subject to any disclaimer, the term of this patent is extended or adjusted under 35 U.S.C. 154(b) by 0 days.

(21) Appl. No.: 18/226,767

(22) Filed: Jul. 26, 2023

(65) Prior Publication Data

US 2024/0018117 A1 Jan. 18, 2024

Related U.S. Application Data

(63) Continuation-in-part of application No. PCT/US2023/013928, filed on Feb. 27, 2023.

(60) Provisional application No. 63/314,823, filed on Feb. 28, 2022.

(51) Int. Cl.

| | |
|---|---|
| ***C07D 317/58*** | (2006.01) |
| ***A61K 45/06*** | (2006.01) |
| ***C07D 327/04*** | (2006.01) |

(52) U.S. Cl.

CPC ............ *C07D 317/58* (2013.01); *A61K 45/06* (2013.01); *C07D 327/04* (2013.01)

(58) Field of Classification Search

CPC ............................ C07D 317/58; C07D 327/04

See application file for complete search history.

(56) References Cited

U.S. PATENT DOCUMENTS 7,060,847 B2 6/2006 Ghoshal et al.

FOREIGN PATENT DOCUMENTS

| | | | | |
|---|---|---|---|---|
| WO | WO-2023283373 | A1 * | 1/2023 |
| WO | 2023056102 | A1 | 4/2023 |
| WO | WO-2023156453 | A1 * | 8/2023 |

OTHER PUBLICATIONS

UBCHEM, SID 381995033, Modify Date: Sep. 8, 2021 [retrieved on Apr. 17, 2023]. Retrieved from the Internet: https://pubchem.ncbi.nlm.nih.gov/substance/381995033 Sep. 8, 2021.

UBCHEM, SID 472178765, Modify Date: Oct. 11, 2022 [retrieved on May 23, 2023J.'Retrieved from the Internet: <URL: https://pubchem.ncbi.nlm.nih.gov/substance/472178765> entire document Oct. 11, 2022.

International Search Report Feb. 7, 2024.

International Search Report and Written Opinion in International Application No. PCT/US23/13928 received on Feb. 7, 2024, 26 pages.

* cited by examiner

*Primary Examiner* — Matthew P Coughlin

(74) *Attorney, Agent, or Firm* — Berg Hill Greenleaf Ruscitti LLP

(57) ABSTRACT

The present invention includes a novel class of MDMA carbamates that can be activated in vivo as prodrugs. The MDMA prodrugs of the invention are enzymatically cleaved in vivo and produce alcohols of low toxicity that are well tolerated and metabolized in humans.

19 Claims, No Drawings

PRODRUG COMPOUNDS OF 3,4-METHYLENEDIOXYMETHAMPHETAMINE (MDMA) AND METHODS OF SYNTHESIZING THE SAME

CROSS-REFERENCE TO RELATED APPLICATIONS

This application is a bypass continuation-in-part of International PCT Application No. PCT/US2023/013928, filed Feb. 27, 2023, which claims the benefit of and priority U.S. Provisional Application No. 63/314,823, filed Feb. 28, 2022. The entire specification, claims, and figures of the above-referenced application is hereby incorporated, in its entirety by reference.

TECHNICAL FIELD

The present invention is directed to novel chemical compositions of matter, and in particular novel MDMA prodrug carbamate compounds having unique pharmacokinetic characteristics.

BACKGROUND 3,4-methylenedioxymethamphetamine (MDMA), is an important experimental psychoactive drug with potential in the supervised treatment of various psychological disorders, including post-traumatic stress disorder (PTSD) and related psychological trauma among other therapeutic uses. MDMA. Rac-MDMA, also generally referred to herein as MDMA, has two enantiomers, S-MDMA and R-MDMA.

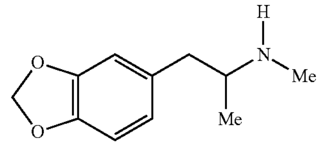

Rac-MDMA

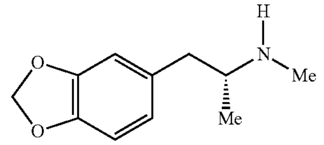

R-MDMA

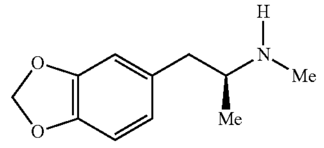

S-MDMA

Chemical formula for racemic MDMA, including R and S forms.

A limited number of basic MDMA carbamates have been synthesized and reported (. These basic compounds were prepared by forensic scientists in order to document the appearance of "masked" MDMA. These were basic MDMA carbamates prepared as analytical standards by forensic scientists. It was believed that these "masked" molecules were designed to evade DEA inspection and would be converted to unmasked MDMA by chemical treatments well known to synthetic organic chemistry. Despite these limitations and elicit motivations by others, there exists a great number of therapeutic and other medically viable options for more complex MDMA carbamates. To address these concerns, there exists a need for novel MDMA carbamates that can be enzymatically activated in vivo, and thereby provide the therapeutic benefits of MDMA in a safe and effective manner. Such novel compositions may offer enhanced pharmacokinetic properties, including improved duration of action for therapeutic dosing in clinical settings, as well as enhanced lipophilicity.

The present invention relates to the use of linear carbinols $C_2$-$C_{18}$ to create never-before reported novel MDMA carbamates that can be activated in vivo as prodrugs. Contrary to the prior basic MDMA carbamates, the MDMA prodrugs of the present invention, are prepared to be enzymatically cleaved and produce alcohols of low toxicity and reported to be both well tolerated and metabolized.

SUMMARY OF THE INVENTION

The present invention includes novel MDMA prodrug carbamate compounds. In a preferred aspect, the novel MDMA prodrug carbamate compounds may include the compounds of Formulas I-V, (also referred to as a/the compound(s) or composition(s) of the invention, or MDMA prodrug), or a pharmaceutically acceptable salt, solvate, stereoisomer, tautomer, or prodrug thereof as described herein.

In one aspect, the MDMA prodrug carbamates of the invention may exhibit increased enhance dermal permeation due to their high lipophilicity. Cleavage to the parent active MDMA may occur in the skin, liver and circulation by carboxyesterases. In this manner, the onset of MDMA action would be determined by the rate of permeation and release in the body. Further, the MDMA prodrug carbamates of the invention allow onset of drug action from dermal application to be sustained at an even rate. This delivery strategy allows longer duration and avoidance of sudden $C_{max}$ serum concentrations.

In one aspect, the MDMA prodrug carbamates of the invention dosed orally, which may delay action of the compound's effect on a subject, but can results in a longer duration of action from the parent dosed orally. This slower onset and more even distribution of the compound's action can be useful in preventing the illicit use of compounds of the invention as the delay in onset and more sustained action would discourage abuse. The action of the MDMA prodrug carbamates of the invention can also allow easier formulation as a patch, being hydrophobic and the linear unsaturated nature of the alcohol portion should provide for greater shelf stability and resistance to oxidation and degradation. As noted below, alcohols higher than $C_{18}$ may be encompassed within eh scope of the invention, as well as branched alcohols, however in a preferred embodiment, the chain length of a linear alcohol may be less than or equal to 18 carbons.

Additional aspects of the invention may become evident based on the specification and figures presented below.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The present invention discloses methods and compositions directed to a novel prodrug approach for modification of MDMA. The novel methods and compositions may include novel prodrug modifications to both the racemic forms of MDMA (Racemic 3,4-methylenedioxymethamphetamine (rac-MDMA) (generally referred to herein as MDMA), as well as enantiopure forms of R-MDMA and S-MDMA and mixtures of the same.

In one preferred embodiment shown below, MDMA is modified at the side chain nitrogen where the single hydrogen is replaced with a carbamoyl group having linear alcohols varying ideally from $R^1$ of carbon length of $C_2$ (ethyl) to $C_{18}$ octadecanyl. The X group is independently sulfur or oxygen, which can provide efficient cleavage in vivo vitro by esterase enzymes.

(I)

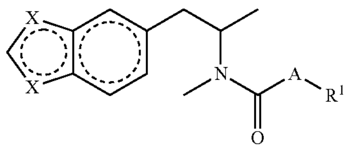

The structure above shows the base scaffold compound (Formula I) for a novel prodrug carbamates of MDMA. In a preferred embodiment, X is independently sulfur or oxygen and $R^1$ is preferably a linear hydrocarbon between $C_1$-$C_{18}$ and/or higher, and A is preferably oxygen. Notably, the dashed lines represents possible double bond positions according to the configuration of X being independently S or O.

In one preferred embodiment, the present invention include a novel MDMA prodrug carbamate according to Formula (I), or a stereoisomer, or pharmaceutically acceptable salt thereof:

(I)

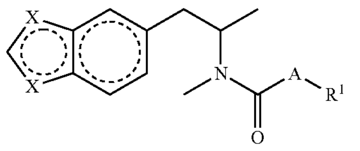

wherein,

X is independently O or S;

A is O;

$R^1$ is alkyl, not $C_2$; and wherein said dashed lines represents possible double bond positions according to the configuration of X being independently S or O.

In another preferred embodiment, the present invention include a novel MDMA prodrug carbamate according to Formula (I), or a stereoisomer, or pharmaceutically acceptable salt thereof:

(I)

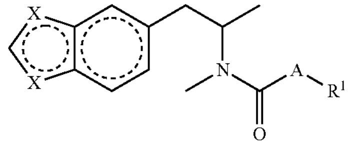

wherein,

X is independently O or S;

A is O;

$R^1$ is $C_2$-$C_{18}$ linear alkyl; and wherein said dashed lines represents possible double bond positions according to the configuration of X being independently S or O.

In another preferred embodiment, the present invention include a novel MDMA prodrug carbamate according to Formula (I), or a stereoisomer, or pharmaceutically acceptable salt thereof:

(I)

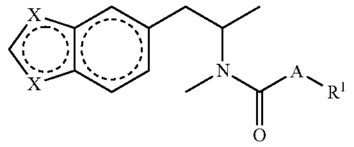

wherein,

X is independently O or S;

A is O;

$R^1$ is $C_2$-$C_x$ linear alkyl, wherein x is between 2-18, or greater than 18; and wherein said dashed lines represents possible double bond positions according to the configuration of X being independently S or O.

In another preferred embodiment, the present invention include a novel MDMA prodrug carbamate according to Formula (I), or a stereoisomer, pharmaceutically acceptable salt thereof:

(I)

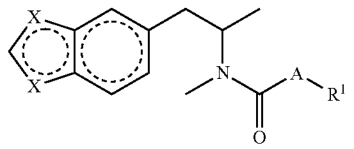

wherein,

X is independently O or S;

A is O;

$R^1$ is selected from the group consisting of: -ethyl, n-proply, n-butyl, n-pentyl, n-hexyl, n-heptyl, n-octyl, n-nonyl, n-decyl, n-undecanyl, n-dodecanyl, n-tridecanyl, n-tertadecanyl, n-pentadecanyl, n-hexadecanyl, n-heltadecanyl, and n-octadecanyl; and wherein said dashed lines represents possible double bond positions according to the configuration of X being independently S or O.

In a preferred embodiment, the present invention include a novel MDMA prodrug carbamate according to Formula (I), or a stereoisomer, pharmaceutically acceptable salt thereof:

(I)

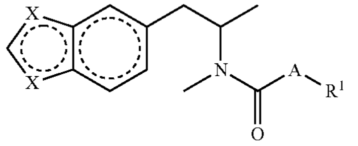

wherein,

X is independently O or S;

A is O;

$R^1$ is selected from the group consisting of CH2CH3,

, 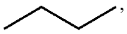, 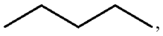, 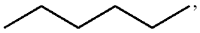, 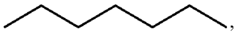, 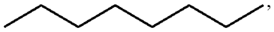, 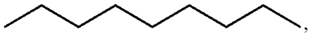, 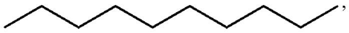, 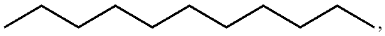, 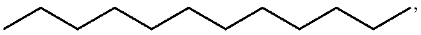, 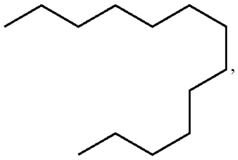, 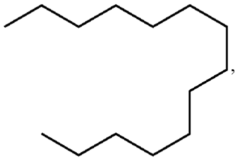, 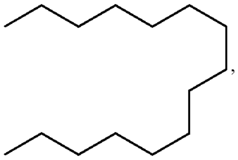, 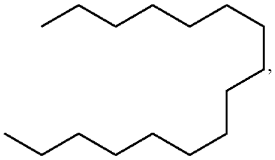, 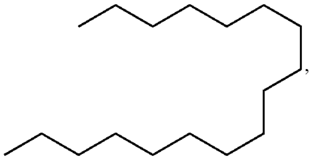, 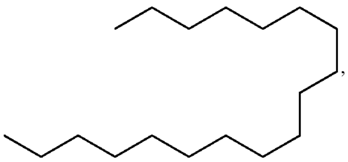 [SMILES: CCCCCCCCCCCCCCCCCC]

and wherein said dashed lines represents possible double bond positions according to the configuration of X being independently S or O.

In a preferred embodiment, the present invention include a novel MDMA prodrug carbamate according to Formula (II), or a stereoisomer, pharmaceutically acceptable salt thereof:

(II)

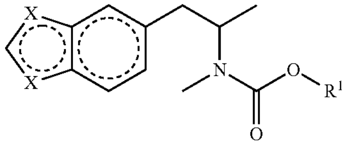

wherein,

X is independently O or S;

$R^1$ is alkyl, not $C_2$; and wherein said dashed lines represents possible double bond positions according to the configuration of X being independently S or O.

In another preferred embodiment, the present invention include a novel MDMA prodrug carbamate according to Formula (II), or a stereoisomer, or pharmaceutically acceptable salt thereof:

(II)

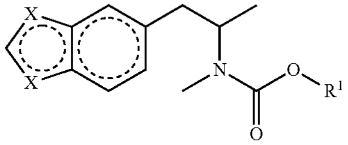

wherein,

X is independently O or S; and $R^1$ is $C_2$-$C_{18}$ linear alkyl; and wherein said dashed lines represents possible double bond positions according to the configuration of X being independently S or O.

In another preferred embodiment, the present invention include a novel MDMA prodrug carbamate according to Formula (II), or a stereoisomer, or pharmaceutically acceptable salt thereof:

(II)

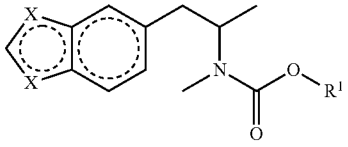

wherein,

X is independently O or S;

$R^1$ is $C_2$-$C_x$ linear alkyl, wherein x is between 2-18, or greater than 18; and wherein said dashed lines represents possible double bond positions according to the configuration of X being independently S or O.

In another preferred embodiment, the present invention include a novel MDMA prodrug carbamate according to Formula (II), or a stereoisomer, pharmaceutically acceptable salt thereof:

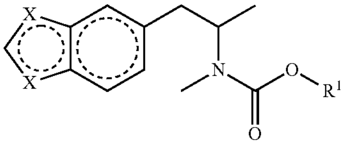

(II)

wherein,

X is independently O or S;

$R^1$ is selected from the group consisting of: -ethyl, n-proply, n-butyl, n-pentyl, n-hexyl, n-heptyl, n-octyl, n-nonyl, n-decyl, n-undecanyl, n-dodecanyl, n-tridecanyl, n-tertadecanyl, n-pentadecanyl, n-hexadecanyl, n-heltadecanyl, and n-octadecanyl; and wherein said dashed lines represents possible double bond positions according to the configuration of X being independently S or O.

In a preferred embodiment, the present invention include a novel MDMA prodrug carbamate according to Formula (II), or a stereoisomer, pharmaceutically acceptable salt thereof:

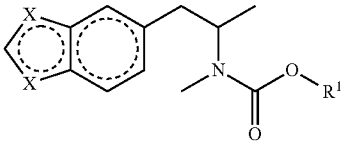

(II)

wherein,

X independently O or S; and $R^1$ is selected from the group consisting of:

CH2CH3,

,
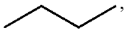,
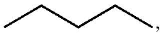,
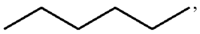,
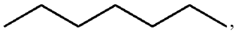,
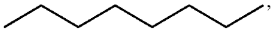,
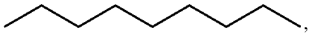,
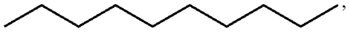,
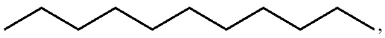,
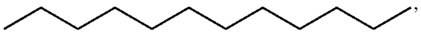,
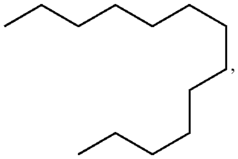,
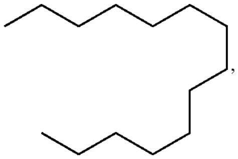,
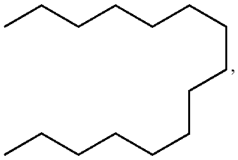, -continued

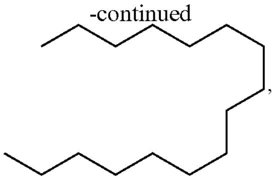,

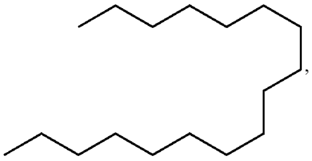,

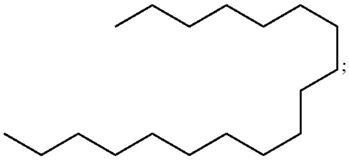 [SMILES: CCCCCCCCCCCCCCCCCC];

and wherein said dashed lines represents possible double bond positions according to the configuration of X being independently S or 0.

In a preferred embodiment, the present invention include a novel MDMA prodrug carbamate according to MY100C5 (Formula III), or a stereoisomer, or pharmaceutically acceptable salt thereof:

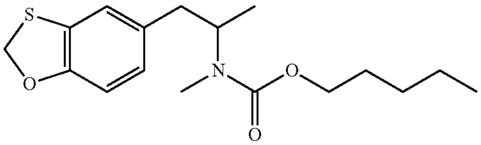

(III)

MY100C5

In a preferred embodiment, the present invention include a novel MDMA prodrug carbamate according to MY200C5 (Formula IV), or a stereoisomer, or pharmaceutically acceptable salt thereof:

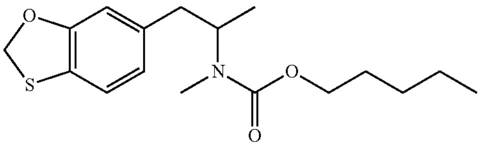

(IV)

MY200C5

In a preferred embodiment, the present invention include a novel MDMA prodrug carbamate according to MY307 (Formula V), or a stereoisomer, or pharmaceutically acceptable salt thereof:

(V)

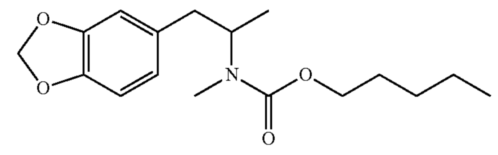

MY307

In another embodiments, the present invention includes novel MDMA prodrug carbamate identified herein as the compound according to Formulas I-V, (also referred to as a/the compound(s) or composition(s) of the invention, or MDMA prodrug), or a pharmaceutically acceptable salt, solvate, stereoisomer, tautomer, or prodrug thereof as described herein. Additional embodiments of the current invention include a compound of Formula I-V, or a pharmaceutically acceptable salt, solvate, stereoisomer, tautomer, or prodrug thereof, for use in recreational, phycological, or medical therapies.

Additional embodiments of the present invention provides systems, methods, and compositions for novel MDMA prodrug according to the compounds of Formula I-V, and a pharmaceutically acceptable carrier or diluent, which may preferably further include a method of treatment of the human or animal body using one or more of the novel compounds, or pharmaceutical compositions described herein.

Additional embodiments of the present invention provide a method for treating a disease or condition comprising: administering to a subject in need thereof, a therapeutically effective amount of a one or more MDMA prodrugs of the invention according to Formulas I-V, or a pharmaceutically composition containing a therapeutically effective amount of a one or more compounds of the invention according to Formulas I-V and a pharmaceutically carrier.

Additional embodiments of the invention include pharmaceutical compositions comprising one or more MDMA prodrugs of the invention according to Formulas I-V. In this preferred embodiment, the novel MDMA prodrugs of the invention, and preferably the MDMA prodrugs according to the compounds of Formula I-V, modulate a serotonin receptors in a subject, and preferably a human subject. In this embodiment, the compounds of Formula I-V are indirect serotonin receptor agonists. As used herein, a "serotonin receptor agonists" means a substance, and preferably a compound of the invention, having the function of acting directly or directly on a serotonin receptor causing an increase in amount of serotonin released into the synapses of a subject. As used herein, an "agonist" means a substance, and preferably a compound of the invention, having the function of binding/activating to a receptor or to produce a biological response. In another embodiment, the present invention provides the use of one or more of the novel MDMA prodrugs according to the compounds of Formula I-V to increase release of dopamine and noradrenaline or inhibit monoamine re-uptake and delay metabolism by inhibition of monoamine oxidase in a subject.

In another embodiment, the present invention provides the use of one or more of the novel MDMA prodrugs according to the compounds of Formula I-V for the treatment of a disease or condition, and preferably a disease or condition in a subject that is may be treated by activating of one or more serotonin receptors by the agonist action of one or more compounds of the invention in a subject in need thereof.

In another embodiment, the present invention provides the use of one or more of the novel MDMA prodrugs according to the compounds of Formula I-V for the treatment of a disease or condition, and preferably a disease or condition in a subject that is may be treated by increasing levels of dopamine or monoamine through the action of one or more compounds of the invention in a subject in need thereof.

A compound of Formula I-V, or a pharmaceutically acceptable salt thereof, for use in the modulation of serotonin receptor activity in research, pharmaceutical, and biotechnology development. A compound of Formula I-V, or a pharmaceutically acceptable salt thereof, for use in the treatment of a disease or condition in which modulation of serotonin receptor activity is beneficial.

Additional embodiments of the invention include methods for treating a disease or condition for which comprising: administering to a subject in need thereof, a therapeutically effective amount of a combination comprising a compound of Formula I-V, or a pharmaceutically acceptable salt thereof, and at least one further therapeutic agent, wherein said further therapeutic agent is selected from the group consisting of: 1) a tryptamine compound, or a tryptamine compound and an entactogen. As used herein, "tryptamine" means compounds having affinity for a serotonin receptor and may include, but not be limited to: substituted tryptamines, psilocybin, psilocin, N,N-dimethyltryptamine, 5-methoxy-N,N-dimethyltryptamine, N,N-Dipropyltryptamine, 5-methoxy-N,N-Dipropyltryptamine, baeocystin ([3-[2-(methylamino)ethy 1]-1H-indol-4-yl] di hydrogen phosphate), norbaeocystin ([3-(2-aminoethyl)-1H-indol-4-yl] dihydrogen phosphate), aeruginascin (N,N,N-trimethyl-4-phosphorl-oxytryptamine), 4-acetoxy-N,N-dimethyltryptamine, 3-(2'-dimethylaminoethy 1)-4-acetoxy-indole. As used herein, "entactogens" means a compounds having the effect of releasing serotonin, norepinephrine and dopamine such as 3,4-methylenedioxyamphetamine (MDMA), 2,5-dimethoxy-4-bromophenethylamine, 3,4-methylenedioxyN-ethylamphetamine, a-lfamethyltryptamine and alpha-ethyltryptamine.

Additional embodiments of the invention include a pharmaceutical composition comprising a compound of Formula I-V, or a pharmaceutically acceptable salt thereof, for use in the treatment of a disease or condition in a subject in need thereof. A compound of the invention or pharmaceutical composition comprising the compound may be administered to a "subject," and preferably a human subject, by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. The subject may be a eukaryote, an animal, a vertebrate animal, a mammal, a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), an ape (e.g., gorilla, chimpanzee, orangutang, gibbon), or a human.

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilizers, preservatives, lubricants, or other materials well known to those skilled in the art and optionally other therapeutic or prophylactic agents.

Thus, the present invention further provides pharmaceutical compositions, as defined below, and methods of making a pharmaceutical composition comprising admixing at least one active compound, as defined above, together with one or more pharmaceutically acceptable carriers, excipients, buffers, adjuvants, stabilizers, or other materials, as described herein.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition). The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt. For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned above are meant to comprise the therapeutically active non-toxic acid and base addition salt forms which the compounds can form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic, and like acids. Conversely, these salt forms can be converted into the free base form by treatment with an appropriate base. The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g., the lithium, sodium, potassium, magnesium, calcium salts and the like, salts with organic bases, e.g., the benzathine, N-methyl-D-glucamine, hydrabamine salts, and salts with amino acids such as, for example, arginine, lysine, and the like. Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary, shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrants will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet. Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents. Exemplary tablets contain up to about 80 wt % drug, from about 10 wt % to about 90 wt % binder, from about O wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated. The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety. Solid formulations for oral administration may be formulated to be immediate and/or modified release. Modified release formulations include delayed-, sustained-, pulsed-, controlled, targeted and programmed release. Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate. Formulations suitable for vaginal administration may be presented as pessaries, tampons, creams, gels, pastes, foams, or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 g/ml, for example from about 10 ng/ml to about 1 g/ml. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 g to about 250 mg per kilogram body weight of the subject per day. Where the active compound is a salt, an ester, prodrug, or the like, the amount administered is calculated on the basis of the parent compound and so the actual weight to be used is increased proportionately.

Additional embodiments of the invention include enzymatically activating one or more MDMA prodrugs of the invention. In this preferred embodiment one or more MDMA prodrugs of the invention, and preferably one or more MDMA prodrugs of the invention according to Formulas I-V, are contacted with a carboxyesterase enzyme that may cleave the R1 group and reconstitute the parent compound. In a preferred embodiment, the step of contacting may occur in vitro, while in alternative embodiment the step of contacting may occur in vivo, for example in the tissues, skin, or gut of a subject of need there.

In one embodiment, the invention includes methods of synthesizing a MDMA prodrug carbamate. According to Scheme 1, a parent MDMA compound is dissolved in a non-reactive solvent such as (Tetrahydrofuran) THF or dichloromethane and treated with phosgene or alternatively a phosgene equivalent such as triphosgene, 1,1'-carbonyldiimidazole or bis(4-nitrophenyl) carbonate to produce in situ the activated carbamate (scheme 1). The active carbamate may be reacted with an alcohol, forming an MDMA carbamate prodrug as described herein. In a preferred embodiment, the step of reacting with an alcohol, may include reacting the active carbamate MDMA compound with an alcohol, and preferably a linear $C_2$-$C_{18}$ alcohol. Alternative embodiments may further include reacting the intermediate MDMA compound with an alcohol greater than $C_{18}$, and preferably a linear alcohol greater than $C_{18}$.

In the above described embodiment, the $C_2$-$C_{18}$ alcohol that reacts with the intermediate MDNA compound may be selected from the group consisting of: ethanol, n-propanol, n-butanol, n-pentanol, n-hexanol, n-heptanol, n-octanol, n-nonanol, n-decanol, n-undecananol, n-dodecananol, n-tridecananol, n-tertadecananol, n-pentadecananol, n-hexadecananol, n-heltadecananol, and n-octadecananol. The carbon atoms in the alcohols are preferably straight, but may alternatively be branched or cyclic in some alternative embodiments.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention. The term "stereoisomer" refers to a molecule that is an enantiomer, diastereomer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

As used herein the singular forms "a", "an", and "the" include plural referents unless the context clearly dictates otherwise. Thus, for example, reference to "a compound" includes a plurality of such compounds, and reference to "the method" includes reference to one or more methods, method steps, and equivalents thereof known to those skilled in the art, and so forth.

Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting. The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ± a range of up to 20%, up to 15%, up to 10%, up to 5%, or up to 4%, 3%, 2%, or 1% compared to the specifically recited value.

The term "compound," "active compound," or "composition," or "compound of the invention" includes all solvates, complexes, polymorphs, radiolabeled derivatives, tautomers, stereoisomers, and optical isomers of the novel MDMA prodrug compounds generally described herein, and salts thereof, unless otherwise specified.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc. It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999). For example, a hydroxy group may be protected as an ether (—OR) or an ester (—OC(═O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(═O)CH3, —OAc).

It may be convenient or desirable to prepare, purify, and/or handle the active compound in the form of a prodrug. The term "prodrug", as used herein, pertains to a compound which, when metabolized (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required. Examples of such metabolically labile esters include, but are not limited to, those wherein R is $C_{1-18}$ alkyl, or an alkyl that is greater than Cis.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-group s/substituents include alkyl groups, hydroxyl groups, alkoxy groups, acyloxy groups, mercapto groups, and aryl groups.

As used herein the term "duration of action" means the time period after administration of one or more of the compounds of the invention during which a physiological, psychological therapeutic response is present in a subject, and preferably a human subject. Generally, the duration of action of one or more of the compounds of the invention is dependent on multiple factors, including subject, does and pharmacokinetic actions within the body as well as metabolic clearance time.

The term "modulation" as used herein in the context of serotonin, or other receptor binding, refers to a change in activation state as compared to the absence of a compound of the invention, or a patent compound of one or more of the compounds of the invention.

The term “beneficial” as used herein in the context of treating a condition, refers to extended relieve of symptoms (duration) and/or a more significant reduction of symptoms (magnitude).

As used herein, a “therapeutically effective amount” for treating or preventing one or more symptoms of a disease or condition, which may preferably include, but not be limited to: for schizophrenia, a therapeutically effective amount is an amount which causes a significant reduction in psychopathology as determined by clinical improvement; for depression, a therapeutically effective amount is an amount that leads to stabilization and remission of symptoms as measured by the Patient Health Questionnaire-9; for OCD, a therapeutically effective amount is an amount that leads to stabilization and remission of symptoms as measured by the Yale-Brown Obsessive Compulsive Scale; for ADHD, a therapeutically effective amount is an amount that leads to stabilization and remission of symptoms as measured by either the ADHD Rating Scale V or ADHD Self-Report Scale; for eating disorders, a therapeutically effective amount is an amount that leads to stabilization and remission of symptoms as measured by the Eating Disorder Examination Questionnaire; for autism spectrum disorders a therapeutically effective amount is an amount that leads to stabilization and remission of symptoms as measured by physicians’ assessment; for PTSD a therapeutically effective amount is an amount that leads to stabilization and remission of symptoms as measured by the Clinician-Administered PTSD Scale for DSM-5; for anxiety, a therapeutically effective amount is an amount that leads to stabilization and remission of symptoms as measured by the General Anxiety Disorder-7; for addiction, a therapeutically effective amount is an amount that leads to stabilization and remission of symptoms as measured by physicians’ assessment; for cluster headaches, a therapeutically effective amount is an amount that leads to stabilization and remission of symptoms as measured by the Cluster Headache Severity Scale (CHSS); for dementia, a therapeutically effective amount is an amount that leads to stabilization and remission of symptoms as measured by the Dementia Rating Scale (DRS); for Alzheimer’s disease, a therapeutically effective amount is an amount that leads to stabilization and remission of symptoms as measured by the Alzheimer’s Disease Assessment Scale-Cognitive Subscale (ADAS-Cog); for paralysis, a therapeutically effective amount is an amount that leads to stabilization and remission of symptoms as measured by physicians’ assessment.

The term “treatment” or “treating”, as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

As used herein, “carboxyesterases” are defined as enzymes that naturally have catalytic activity toward the hydrolysis of carboxyesters which results in the formation of an organic acid and an alcohol.

As used herein, the term “alcohol” means an alcohol that comprises a $C_{1-12}$ alkyl moiety substituted at a hydrogen atom with one hydroxyl group. Alcohols include methanol, ethanol, n-propanol, n-butanol, n-pentanol, n-hexanol, n-heptanol, n-octanol, n-nonanol, n-decanol, n-undecananol, n-dodecananol, n-tridecananol, n-tertadecananol, n-pentadecananol, n-hexadecananol, n-heltadecananol, and n-octadecananol. The carbon atoms in alcohols can be straight, branched or cyclic. Alcohol includes any subset of the foregoing, for example $C_{1-18}$ alcohols (alcohols having 1-18 carbon atoms). Additional embodiment include $C_1$, alcohols, where x is greater than 18. (alcohols having greater than 18 carbon atoms) In the context of the present invention, $C_1$-$C_{18}$-alkyl represents a linear or branched $C_1$-$C_{18}$-alkyl radical, for example methyl, -ethyl, n-proply, n-butyl, n-pentyl, n-hexyl, n-heptyl, n-octyl, n-nonyl, n-decyl, n-undecanyl, n-dodecanyl, n-tridecanyl, n-tertadecanyl, n-pentadecanyl, n-hexadecanyl, n-heltadecanyl, and n-octadecanyl.

As used herein, the term “carbamate” is meant a group, when a hydroxyl protecting group, having the formula —OC(O)NR2, or, when an amine protecting group, having the formula NR'—C(O)OR, where each R and R' is independently H, optionally substituted alkyl, optionally substituted alkenyl, optionally substituted aryl, or optionally substituted arylalkyl.

As used herein, “lipophilicity” refers to the tendency of a compound to partition between a lipophilic organic phase and a polar aqueous phase. In drug development lipophilicity of a compound is represented either as partition coefficient, log P or distribution coefficient, log D.

Phosgene means the organic chemical compound with the formula $COCl_2$. Triphosgene means a chemical compound with the formula $OC(OCCl_3)_2$. Phosgene equivalents for synthesis of MDMA prodrug carbamates as described herein are provided below:

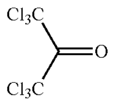

Triphosgene

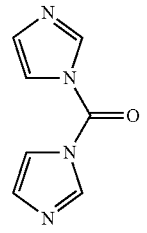

1,1'-carbonyldiimidazole

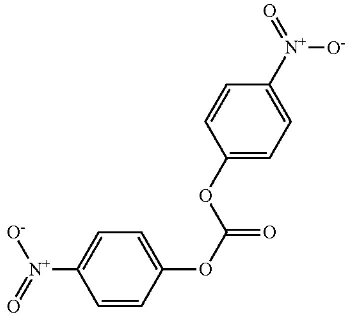

Bis(4-nitrophenyl)carbonate

The invention now being generally described will be more readily understood by reference to the following examples, which are included merely for the purposes of illustration of certain embodiments of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1. Synthesis of MDMA

As shown in Scheme 1 below, the present invention provides for the step-wise synthesis of

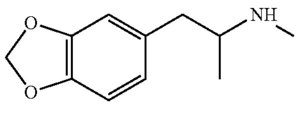

MDMA according to the following scheme:

Scheme 1

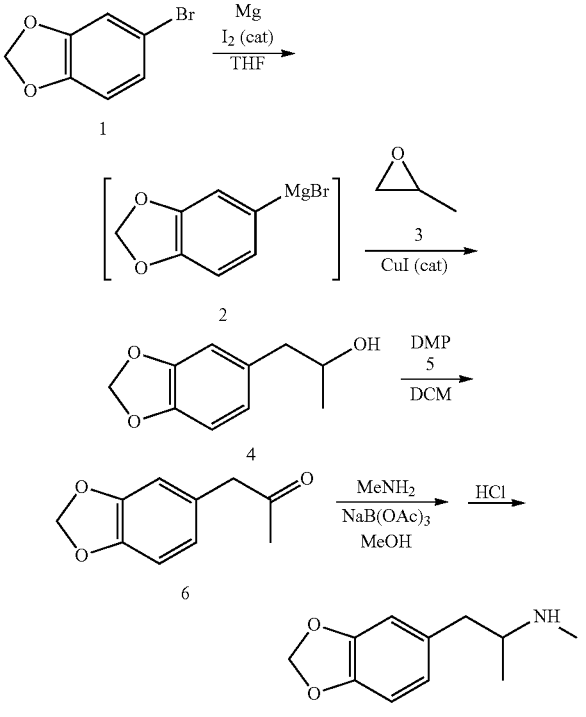

1

2

4

6

MDMA

As described in Scheme 1, the present inventors demonstrated the synthesis of the MDMA precursor compound 1-(benzo[d][1,3]dioxol-5-yl)propan-2-ol (4).

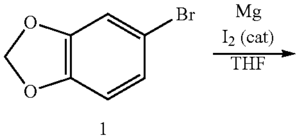

1

-continued

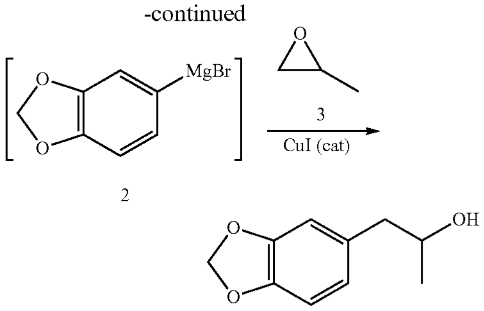

2

4

In this embodiment, to a pre-dried 3-neck 500 mL round bottom flask equipped with a condenser, additional funnel and thermometer under nitrogen was charged magnesium turnings (4.53 g, 186.5 mmol, 1.5 eq.), iodine ($I_2$) (0.1 g, 0.39 mmol, 0.003 eq) and tetrahydrofuran (THF). The solution of 4-bromo-1,2-(methylenedioxy) benzene 1 (25.0 g, 124.3 mmol, 1 eq) in THF (100 mL) was added via the additional funnel. The reaction mixture was heated at 60° C. to 70° C. for 1 hour, cooled to room temperature. To the Grignard reagent solution 2 was added 2-methyloxirane 3 (13.1 mL, 186.5 mmol, 1.5 eq), copper iodide (CuI) (1.18 g, 6.22 mmol, 0.05 eq) and anhydrous THF (100 mL) at 0° C. to 5° C. The resultant mixture was stirred at 0° C. and brought to room temperature over 16 hours while stirring. The reaction mixture was cooled to 0° C. to 5° C., quenched with a cold solution of acetic acid (AcOH, 21.3 mL, 372.9 mmol, 3.0 eq) in water (150 mL) slowly over a period of 20 to 30 minutes while keeping temperature below 25° C. The reaction mixture was diluted with ethyl acetate (EtOAc) (200 mL), sodium chloride (NaCl) solid (50 g) was added and stirred for another 20 to 30 minutes, and the layers were separated. The aqueous layer was extracted EtOAc. The combined organic layer was washed with saturated sodium bicarbonate ($NaHCO_3$) aqueous solution, brine, dried over sodium sulphate ($Na_2SO_4$), filtered, and concentrated under vacuum to afford crude oil product 1-(benzo[d][1,3]dioxol-5-yl)propan-2-ol 4 (22.4 g, quantitative yield) which was used in the next step without further purification. $^1$H NMR (600 MHz, $CDCl_3$): δ 6.78 (d, J=8.4 Hz, 1H), 6.73 (s, 1H), 6.68 (m, 1H), 5.96 (s, 2H), 3.98 (m, 1H), 2.73 (m, 1H), 2.61 (m, 1H), 1.32 (d, J=6.6 Hz, 3H).

As described in Scheme 1, the present inventors further demonstrated the synthesis of the MDMA precursor compound Synthesis of 1-(benzo[d][1,3]dioxol-5-yl)propan-2-one (6).

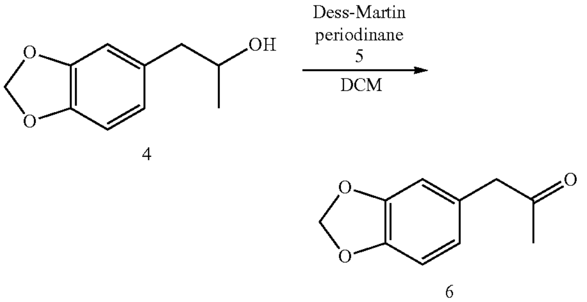

4

6

In this embodiment, to a 3-neck 500 mL round bottom flask equipped with mechanical stirrer and thermometer was charged 1-(benzo[d][1,3]dioxol-5-yl)propan-2-ol 4 (22.4 g, 124.3 mmol, 1 eq) and dichloromethane (DCM) (224 mL, 10 volume). The resultant solution was stirred and cooled to 0° C. to 5° C., and solid Dess-Martin Periodinane (DMP) (55.4 g, 130.5 mmol, 1.05 eq) was added in portions. After the DMP was added completely, the resultant solution was stirred at 0° C. to 5° C. for 1 hour and brought to room temperature over a period 2 hours while stirring, and precipitation formed. The reaction mixture was analyzed by TLC to check the progress of the reaction and confirm the completion of the reaction. The reaction mixture was then cooled to 0° C. to 5° C. and quenched slowly with saturated sodium bicarbonate ($NaHCO_3$) aqueous solution (400 mL) to pH 8, and sodium thiosulfate ($Na_2S_2O_3$) (10 g) was added to quench excess DMP. The resultant suspension was stirred at room temperature for 1 hour, filtered through celite, and rinsed with DCM. The two-layer filtrate was separated, and the aq layer was extracted with DCM. The combined DCM layer was dried over $Na_2SO_4$, filtered, and concentrated under vacuum to give a brown crude oil (25.8 g). The crude oil was stirred in hexanes at 60° C. for 30 minutes and the clear hexanes solution was decanted. The clear solution was concentrated under vacuum to afford 1-(benzo[d][1,3]dioxol-5-yl)propan-2-one 6 (18.7 g, 84% yield) as yellow oil. $^1$H NMR (600 MHz, $CDCl_3$): δ 6.70 (d, J=7.8 Hz, 1H), 6.60 (s, 1H), 6.57 (m, 1H), 5.87 (s, 2H), 3.52 (s, 2H), 2.07 (s, 3H).

As described in Scheme 1, the present inventors further demonstrated the synthesis of the 1-(benzo[d][1,3]dioxol-5-yl)-N-methylpropan-2-amine hydrochloride (MDMA), shown herein as a pharmaceutically acceptable salt:

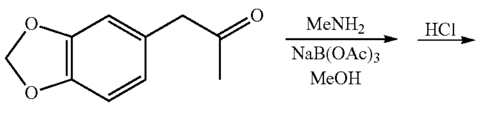

6

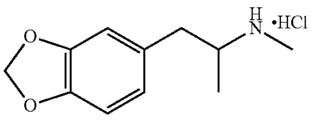

MDMA

In this embodiment, to a3-neck 1 L round bottom flask equipped with mechanical stirrer and thermometer was charged 1-(benzo[d][1,3]dioxol-5-yl)propan-2-one 6 (18.7 g, 104.9 mmol, 1 eq) and methanol (MeOH) (374 mL, 20 volume eq). The resultant mixture was stirred and cooled to 0° C. to 5° C., a solution of 33 wt % methylamine ($MeNH_2$) in ethanol (EtOH) (39.2 mL, 315 mmol, 3 eq) was added slowly, followed by solid by sodium triacetoxy-borohydride ($NaBH(OAc)_3$) (44.5 g, 210 mmol, 2 eq) in portions over a period of 15 to 20 minutes. The resultant mixture was stirred at 0° C. to 5° C. for 2 hours, second portion of 33 wt % $MeNH_2$ in EtOH (13.1 mL, 105 mmol, 1 eq) and NaBH $(OAc)_3$ (22.3 g, 105 mmol, 1 eq) was added slowly. The reaction mixture was stirred at 0° C. to room temperature for 16 hours and analyzed by TLC to check the progress of the reaction and confirm the completion of the reaction. The reaction mixture was diluted with water (250 mL), stirred at room temperature for another 0.5 hour, and concentrated under vacuum to remove organic solvent. The residue was stirred and diluted with water (250 mL), cooled to 0° C. to 5° C., and concentrated HCl aqueous (75 mL, 0.9 mol) was added slowly via an additional funnel over a period of 30 to 40 minutes (pH 1 to 2). The reaction mixture was extracted with EtOAc. The aqueous layer was diluted with DCM (200 mL), stirred, and cooled to 0° C. to 5° C., and a pre-cooled solution of sodium hydroxide (NaOH) (40 g, 1 mol) in water (120 mL) was added slowly via an additional funnel (pH 10 to 11). The layers were separated, and the aqueous layer was extracted with DCM. The combined DCM layer was washed with water, dried over $Na_2SO_4$, filtered, and concentrated under vacuum to give MDMA free base as brown oil (15 g). The crude oil was dissolved in EtOAc (150 mL), cooled to 5° C. to 10° C., and a solution of 1 M HCl in diethyl ether ($Et_2O$) (100 mL, 100 mmol) was added slowly over a period of 15 to 20 minutes via an additional funnel. The resultant suspension was stirred at room temperature for 16 hours, filtered, washed with EtOAc, dried in air to give crude MDMA HCl salt (16.7 g) as a brown solid, which was recrystalized in EtOH to afford MDMA HCl salt (10.0 g, 41% yield) as off-white solid. mp: 148° C. to 150° C. $^1$H NMR (600 MHz, $D_2O$): d 6.68 (d, J=7.8 Hz, 1H), 6.78 (d, J=1.2 Hz, 1H), 7.72 (dd, J=1.2 and 7.8 Hz, 1H), 5.90 (s, 2H), 3.42 (m, 1H), 2.91 (dd, J=6.6 and 14.4 Hz, 1H), 2.77 (dd, J=6.6 and 14.4 Hz, 1H), 2.63 (s, 3H), 1.21 (d, J=6.6 Hz, 3H). $^{13}$C NMR (150 MHz, $D_2O$): d 147.5, 146.3, 129.4, 122.7, 109.6, 108.7, 101.1, 56.4, 38.4, 29.8, 14.7.

Example 2. Synthesis of pentyl (1-(benzo[d][1,3]oxathiol-5-yl)propan-2-yl)(methyl)carbamate As shown in Scheme 2 below, the present invention provides for the step-wise synthesis of the compound according to MY1005C (Formula III).

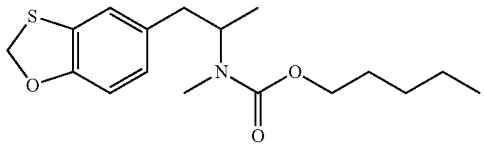

MY100C5 according to the following scheme:

Scheme 2

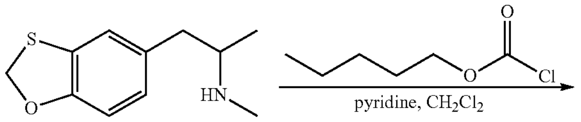

1

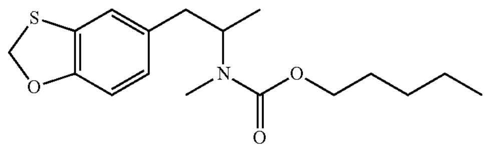

MY100C5

As described in Scheme 2, the present inventors demonstrated the synthesis of pentyl (1-(benzo[d][1,3]oxathiol-5-yl)propan-2-yl)(methyl)carbamate (MY1005C or Formula III). In this embodiment, an ice-cold yellow solution of 1-(benzo[d][1,3]oxathiol-5-yl)-N-methylpropan-2-amine 1 (0.140 g, 0.67 mmol) in dichloromethane (5 mL) was treated with pyridine (0.12 g, 1.52 mmol) followed by dropwise addition of pentyl chloroformate (0.17 g, 1.13 mmol). The mixture was stirred for 30 minutes, then the ice bath was removed and stirred at room temperature overnight. The mixture was diluted with water and extracted with ethyl acetate. The organic extract was dried over sodium sulphate, filtered and concentrated in vacuo to a yellow oil. Column chromatography (silica gel; 0-5% ethyl acetate in hexanes) afforded pentyl (1-(benzo[d][1,3]oxathiol-5-yl)propan-2-yl)(methyl)carbamate MY100C5 (0.136 g) as a colourless oil. The oil was repurified by prep TLC (25% ethyl acetate in hexanes) to obtain pure product as a colourless oil (0.040 g, 19% yield). $^1$H NMR (400 MHz, $CDCl_3$): δ 7.00 (d, J=16.3 Hz, 1H), 6.87-6.71 (m, 1H), 6.74 (d, J=8.0 Hz, 1H), 5.67 (s, 2H), 4.40 (d, J=46.1 Hz, 1H), 4.10-3.94 (m, 2H), 2.84-2.65 (m, 4H), 2.64-2.55 (m, 1H), 1.67-1.52 (m, 2H), 1.43-1.26 (m, 4H), 1.20-1.08 (m, 3H), 0.93 (t, J=6.9 Hz, 3H). $^{13}$C NMR (100 MHz, $CDCl_3$): δ 156.4, 154.7, 133.3, 126.4, 125.8, 122.6, 109.9, 75.2, 65.3, 52.3, 39.9, 39.8, 28.7, 28.2, 27.9, 22.4, 14.0. MS (ESI) m/z: $[M+1]^+$ Calcd for $C_{17}H_{25}NO_3S$ 324.16; Found 324.1. HPLC purity: 96.89%.

Example 3. Synthesis of pentyl (1-(benzo[d][1,3]oxathiol-6-yl)propan-2-yl)(methyl)carbamate As shown in Scheme 3 below, the present invention provides for the step-wise synthesis of the compound according to MY200C5 (Formula IV):

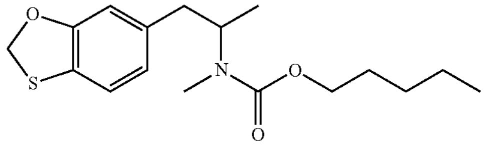

MY200C5 according to the following scheme:

Scheme 3

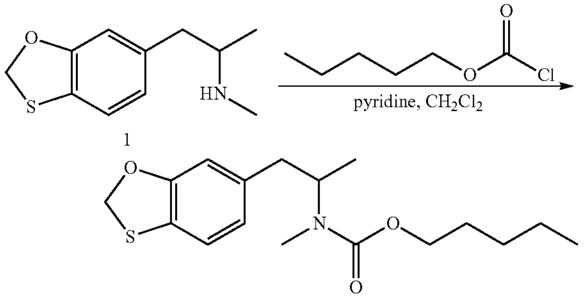

1

MY200C5

As described in Scheme 3, the present inventors demonstrated the synthesis of pentyl (1-(benzo[d][1,3]oxathiol-6-yl)propan-2-yl)(methyl)carbamate (MY200C5). In this embodiment, to a solution of 1-(benzo[d][1,3]oxathiol-6-yl)-N-methylpropan-2-amine 1 (0.093 g, 0.44 mmol) in dichloromethane (5 mL) at 0° C. was pyridine (0.06 mL, 0.79 mmol) added followed by the dropwise addition of pentyl chloroformate (0.11 mL, 0.704 mmol). The reaction was stirred at 0° C. for 30 minutes then raised to room temperature for 1.5 hours. The reaction mixture was transferred to a separatory funnel and washed with water and extracted with ethyl acetate. The organic layer was dried, filtered and concentrated in vacuo. The crude was purified by column chromatography (0-10% ethyl acetate/hexane) to yield pentyl (1-(benzo[d][1,3]oxathiol-6-yl)propan-2-yl)(methyl)carbamate MY200C5 (0.064 g) as a reddish oil. This oil was repurified by prep TLC (20% ethyl acetate in hexanes) to obtain pure product as a brown oil (0.040 g, 28% yield). $^1$H NMR (400 MHz, $CDCl_3$) δ 7.07 (d, J=7.8 Hz, 1H), 6.70 (q, J=12.1, 9.4 Hz, 2H), 5.68 (s, 2H), 4.42 (d, J=48.6 Hz, 1H), 4.02 (s, 2H), 2.76 (d, J=22.5 Hz, 4H), 2.63 (d, J=7.5 Hz, 1H), 1.68-1.53 (m, 2H), 1.40-1.29 (m, 4H), 1.15 (d, J=4.7 Hz, 3H), 0.93 (t, J=7.0 Hz, 3H). $^{13}$C NMR (100 MHz, $CDCl_3$) δ 195.5, 156.3, 137.3, 123, 121.9, 110.9, 75.3, 65.3, 52.2, 40.3, 28.7, 28.1, 28.0, 22.4, 14.0. MS (ESI) m/z: $[M+H]^+$ Calcd for $C_{17}H_{25}NO_3S$ 324.16; found 324.1. HPLC purity: 97.36%.

Example 4. Synthesis of pentyl (1-(benzo[d][1,3]dioxol-5-yl)propan-2-yl)(methyl)carbamate As shown in Scheme 4 below, the present invention provides for the step-wise synthesis of the compound according to MY307 (Formula V):

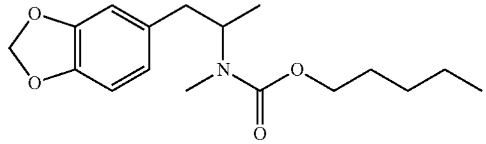

MY307 according to the following scheme:

Scheme 4

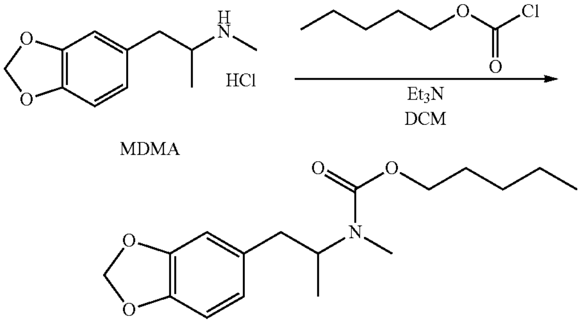

MDMA

MY307

As described in Scheme 5, the present inventors demonstrated the synthesis of pentyl (1-(benzo[d][1,3]dioxol-5-yl)propan-2-yl)(methyl)carbamate (MY307). In this embodiment, to To a suspension of MDMA HCl salt (0.1 g, 0.43 mmol, 1 eq) in DCM (10 mL) at 0° C.~5° C. was added $Et_3N$ (0.12 mL, 0.87 mmol, 2 eq), stirred for 10 min, then pentyl chloroformate (0.08 g, 0.53 mmol, 1.2 eq) was added in portions. The resultant mixture was stirred at 0° C.~5° C. for 1 hour, quenched with sat. $NaHCO_3$ aq, and the layers were separated. The DCM layer was washed with water, dried over $Na_2SO_4$, concentrated under vacuum to afford pentyl (1-(benzo[d][1,3]dioxol-5-yl)propan-2-yl)(methyl)carbamate MY307 (0.116 g, yield 86%) as pale-yellow oil. $^1$H NMR (600 MHz, $CDCl_3$): δ 6.51-6.65 (m, 3H), 5.85 (s, 2H), 4.25-4.39 (m, 1H), 3.91-3.95 (m, 2H), 2.65-2.71 (m, 4H), 2.51-2.53 (m, 1H), 1.47 (m, 2H), 1.23-1.29 (m, 4H), 1.05 (d, J=4.2 Hz, 3H), 0.83 (t, J=6.6 Hz, 3H). $^{13}$C NMR (150 MHz, $CDCl_3$): δ 156.4, 147.5, 145.9, 132.6, 121.8, 109.3(split), 108.1, 65.3 (split), 52.4 (split), 40.3 (split), 28.7, 28.1, 27.9, 22.2 (split), 17.6 (split), 13.9. LCMS m/z=308 $[M+1]^+$ In an alternate embodiment, the present inventors demonstrated the synthesis of pentyl (1-(benzo[d][1,3]dioxol-5-yl)propan-2-yl)(methyl)carbamate (MY307) through the following scheme:

Scheme 4B

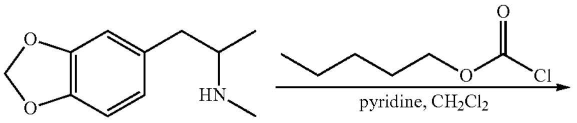

1

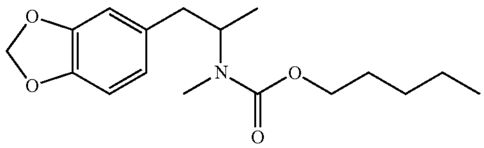

MY307

Example 5: Characteristics of MDMA Prodrug Carbamates

In one embodiment, the invention includes MDMA prodrug carbamates. As noted below, synthesis of one or more of the MDMA prodrug carbamates may use higher weight alcohols, $C_1$-$C_{18}$ alcohol preferred as described below. As noted above, the MDMA prodrug carbamates possess significantly higher Log P values and therefore higher lipophilicity. The novel MDMA prodrug carbamates also blocks the —NH group of the parent MDMA compound with a non-hydrogen donor group. This change in structure gives the MDMA prodrug molecule the ability to permeate tissues, particularly skin, when applied as a cream or liquid formulation. These molecules also possess oral bioavailability and can be dosed orally or injected subcutaneously as a controlled-release depot. Modification also increases the shelf stability and prevents oxidation or degradation of the prodrug. As shown below, the MDMA prodrug of the invention is cleavable in vivo in skin or in the gut via carboxyesterases present in tissues or gut of a subject.

Enzymatic Activation of MDMA Prodrug

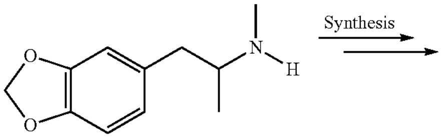

Parent-
rac-MDMA or R,S-MDMA

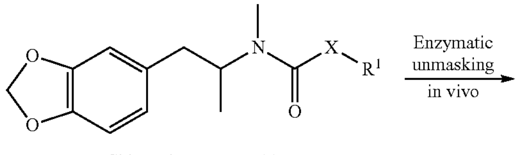

Skin and gut permeable
carbamates

-continued

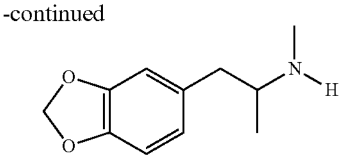

Parent
rac-MDMA or chiral MDMA

Example 2: Synthesis and Cleavage of MDMA Prodrug Carbamates

In one embodiment, the invention includes methods of synthesizing a MDMA prodrug carbamate. According to Scheme 1, MDMA is dissolved in a non-reactive solvent such as (Tetrahydrofuran) THF or dichloromethane and treated with phosgene or ideally a phosgene equivalent such as triphosgene, 1,1'-carbonyldiimidazole or bis(4-nitrophenyl) carbonate to produce in situ the activated carbamate (scheme 1).

Synthesis Scheme 5

Synthesis Scheme 5

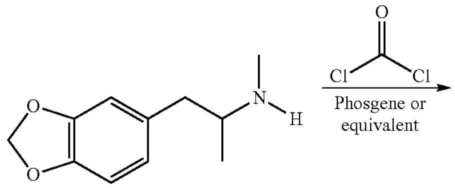

Parent rac-MDMA

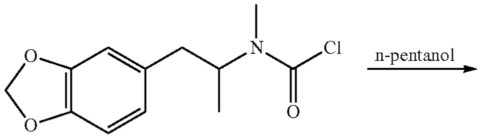

In-situ chlorocarbamyl
chloride

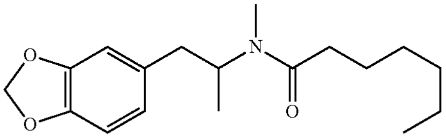

MDMA-pentylcarbamate

The above shows a representative preparation of MDMA prodrug carbamate from phosgene of equivalent and pentanol. Excess alcohol is then added to react with the active carbamate to prepare the desired carbamate. A typical alcohol would be a long chain linear alcohol such as pentanol as shown in scheme 1. In similar manner, any of the linear alcohols from methanol ($C_1$) to octadecanol ($C_{18}$) and higher may be employed.

REFERENCES

1. J. Xu, A. George, H. Salourus, Forensic Chemistry, 2020, 18, 100210.
2. B. Meyer, B. Copp, B. Bogun, G. Miskelly, Drug Testing and Analysis, 2020, 12(4), 524-537.

TABLE 1

| Exemplary $R^1$ Groups for MDMA carbamate prodrugs. | |
|---|---|
| C1 | CH3 (reported, FIG. 3 |
| C2 | CH2CH3 |
| C3 | 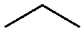 n-propyl |
| C4 | 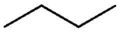 n-butyl |
| C5 | 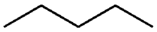 n-pentyl |
| C6 | 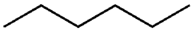 n-hexyl |
| C7 | 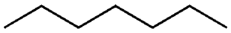 n-heptyl |
| C8 | 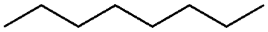 n-octyl |
| C9 | 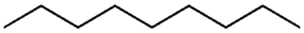 n-nonyl |
| C10 | 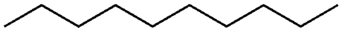 n-decyl |
| C11 | 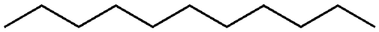 n-undecanyl |
| C12 | 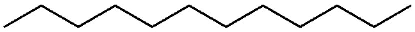 n-dodecanyl |
| C13 | 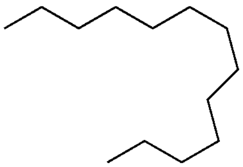 n-tridecanyl |
| C14 | 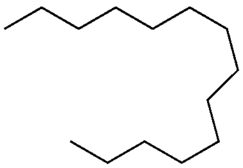 n-tetraecanyl |
| C15 | 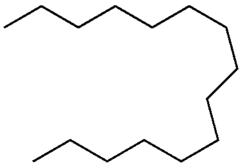 n-pentadecanyl |
| C16 | 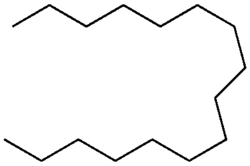 [SMILES: CCCCCCCCCCCCCCCC] n-hexadecanyl |
| C17 | 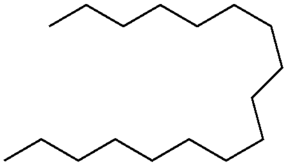 [SMILES: CCCCCCCCCCCCCCCCC] n-heptadecanyl |
| C18 | 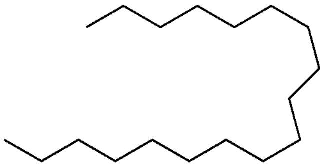 [SMILES: CCCCCCCCCCCCCCCCCC] n-octadecanyl |

What is claimed is:

1. A prodrug compound according to Formula I:

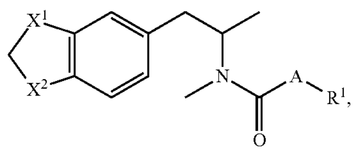

(I)

or pharmaceutically acceptable salt thereof, wherein, $X^1$ is O or S, and when $X^1$ is O then $X^2$ is S;

$X^2$ is O or S, and when $X^2$ is O, then $X^1$ is S;

A is O;

$R^1$ is a $C_5$-$C_{18}$ alkyl.

2. The compound of claim 1, wherein $R^1$ is selected from: n-pentyl, n-hexyl, n-heptyl, n-octyl, n-nonyl, n-decyl, n-undecanyl, n-dodecanyl, n-tridecanyl, n-tertadecanyl, n-pentadecanyl, n-hexadecanyl, n-heptadecanyl, and n-octadecanyl.

3. The compound of claim 1, wherein the compound is a prodrug compound according to Formula III:

(III)

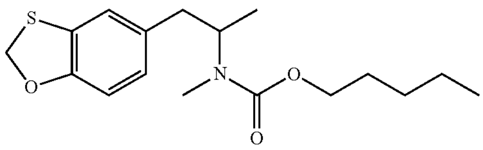

, or pharmaceutically acceptable salt thereof.

4. The compound of claim 1, wherein the compound is a prodrug compound according to Formula IV:

(IV)

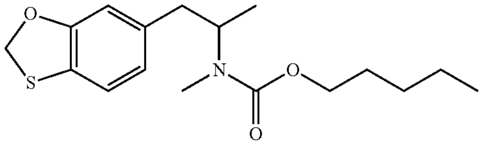

, or pharmaceutically acceptable salt thereof.

5. A pharmaceutical composition comprising the compound of claim 1, and at least one pharmaceutically acceptable carrier.

6. The pharmaceutical composition of claim 5, wherein the pharmaceutical composition comprises a therapeutically effective amount of the compound for the treatment of a disease or condition in which modulation of serotonin receptor activity is beneficial.

7. The pharmaceutical composition of claim 6, wherein said disease or condition is selected from the group consisting of: schizophrenia, addiction, smoking addiction, depression, obsessive compulsive disorder (OCD), cluster headaches, dementia, Alzheimer's disease, paralysis, attention deficit-hyperactivity disorder (ADHD), eating disorders, post-traumatic stress disorder (PTSD), anxiety, and autism.

8. The pharmaceutical composition of claim 1, further comprising at least one further therapeutic agent selected from: a tryptamine compound, an entactogen compound, or a combination of the same.

9. A pharmaceutical composition comprising the compound of claim 3, and at least one pharmaceutically acceptable carrier.

10. The pharmaceutical composition of claim 9, wherein the pharmaceutical composition comprises a therapeutically effective amount of the compound for the treatment of a disease or condition in which modulation of serotonin receptor activity is beneficial.

11. The pharmaceutical composition of claim 10, wherein said disease or condition is selected from the group consisting of: schizophrenia, addiction, smoking addiction, depression, obsessive compulsive disorder (OCD), cluster headaches, dementia, Alzheimer's disease, paralysis, attention deficit-hyperactivity disorder (ADHD), eating disorders, post-traumatic stress disorder (PTSD), anxiety, and autism.

12. The pharmaceutical composition of claim 9, further comprising at least one further therapeutic agent selected from: a tryptamine compound, an entactogen compound, or a combination of the same.

13. A pharmaceutical composition comprising the compound of claim 4, and at least one pharmaceutically acceptable carrier.

14. The pharmaceutical composition of claim 13, wherein the pharmaceutical composition comprises a therapeutically effective amount of the compound for the treatment of a disease or condition in which modulation of serotonin receptor activity is beneficial.

15. The pharmaceutical composition of claim 14, wherein said disease or condition is selected from the group consisting of: schizophrenia, addiction, smoking addiction, depression, obsessive compulsive disorder (OCD), cluster headaches, dementia, Alzheimer's disease, paralysis, attention deficit-hyperactivity disorder (ADHD), eating disorders, post-traumatic stress disorder (PTSD), anxiety, and autism.

16. The pharmaceutical composition of claim 13, further comprising at least one further therapeutic agent selected from: a tryptamine compound, an entactogen compound, or a combination of the same.

17. A compound selected from:

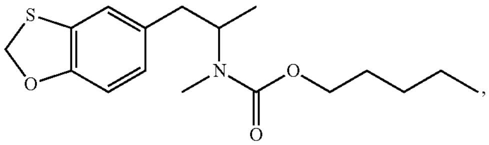 [SMILES: CCCCCOC(=O)N(C)C(C)Cc1ccc2c(c1)SCO2]

,

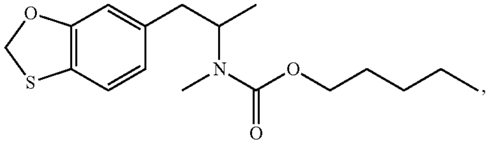 [SMILES: CCCCCOC(=O)N(C)C(C)Cc1ccc2c(c1)OCS2]

, or pharmaceutically acceptable salt thereof.

18. A compound selected from:

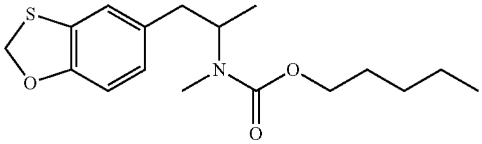

.

19. A compound selected from:

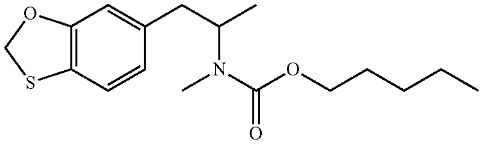

.

* * * * *